United States Patent [19]
Mead et al.

[11] 3,996,785
[45] Dec. 14, 1976

[54] MEANS FOR ON-LINE DETERMINATION OF BOILING POINT PROPERTIES OF CRUDE OIL

[75] Inventors: Theodore C. Mead, Port Arthur; Charles W. Harrison, Nederland; Irene W. Kwan, Houston, all of Tex.

[73] Assignee: Texaco Inc., New York, N.Y.

[22] Filed: Dec. 29, 1975

[21] Appl. No.: 644,473

[52] U.S. Cl. .................................. 73/17 A; 73/53
[51] Int. Cl.² ..................................... G01N 25/08
[58] Field of Search .................... 73/17 A, 53, 61.3

[56] References Cited

UNITED STATES PATENTS

| | | | |
|---|---|---|---|
| 3,239,432 | 3/1966 | Rhodes | 73/53 |
| 3,253,454 | 5/1966 | Neil | 73/17 |
| 3,720,096 | 3/1973 | Woodle | 73/53 |

Primary Examiner—Herbert Goldstein
Attorney, Agent, or Firm—T. H. Whaley; C. G. Ries; Ronald G. Gillespie

[57] ABSTRACT

On-line sensors sense the kinematic viscosity, the infrared absorption, at a predetermined wavelength, and the sulfur content of crude oil and corresponding signals are provided to a computer circuit. The computer circuit solves the equation $M\%BP = -\{C_1 - C_2[\ln(IR \times C_3)] - C_4 S + C_5[\ln(IR \times C_3)]S\} \ln KV$, where $M\%BP$ is a particular percent boiling point property of crude oil, IR is the infrared absorption of the crude oil, S is the sulfur content of the crude oil, KV is the kinematic viscosity of the crude oil, and $C_1$ through $C_5$ are constants.

6 Claims, 7 Drawing Figures

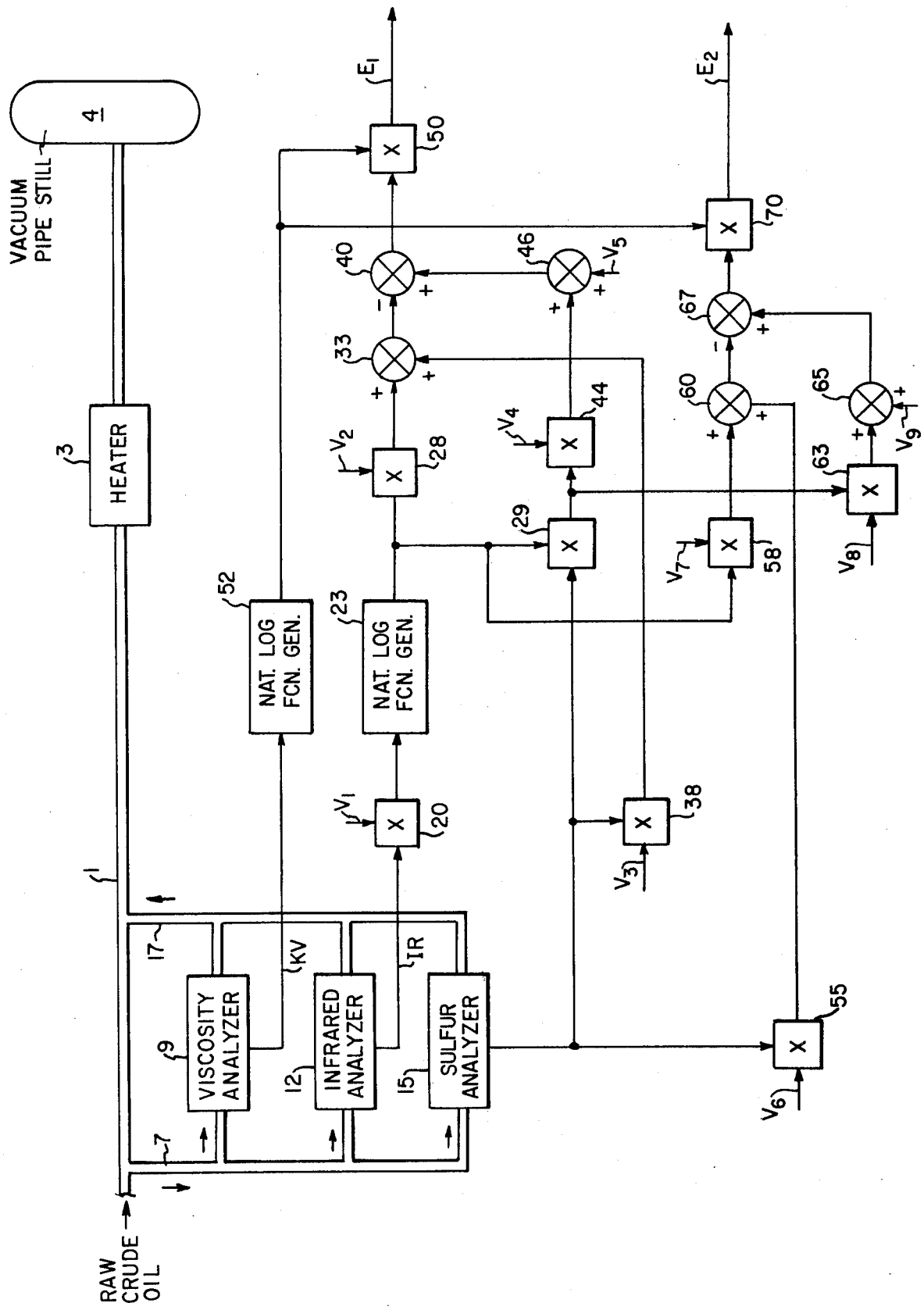

MEANS FOR ON-LINE DETERMINATION OF BOILING POINT PROPERTIES OF CRUDE OIL

BACKGROUND OF THE INVENTION

1. Field of the Invention

The present invention relates to metering systems in general and, more particularly, to systems for determining boiling point properties of crude oil.

2. Description of the Prior Art

Heretofore boiling point properties of crude oil were determined by distillation which required samples to be taken and removed to a laboratory for determination. The present system differs by utilizing an empirically derived equation using three parameters of crude oil which may be analyzed on line so that an on-line boiling point determination can be made.

SUMMARY OF THE INVENTION

An on-line boiling point analyzer which provides a signal corresponding to a particular boiling point property of crude oil flowing in a line, includes analyzers sampling the crude oil and providing signals corresponding to the sulfur content, to the infrared absorption at a predetermined wavelength and to the kinematic viscosity of the crude oil. A circuit provides a signal corresponding to the particular boiling point property of the crude oil in accordance with the signals from the analyzers.

The objects and advantages of the invention will appear more fully hereinafter, from a consideration of the detailed description which follows, taken together with the accompanying drawing wherein one embodiment is illustrated by way of example. It is to be expressly understood, however, that the drawing is for illustrative purposes only and is not to be construed as defining the limits of the invention.

DESCRIPTION OF THE DRAWING

The FIGURE shows crude oil being fed into a vacuum pipe still, shown in partial schematic form, being monitored by an on-line boiling point analyzer, constructed in accordance with the present invention, shown in block diagram form.

DESCRIPTION OF THE INVENTION

The following empirically derived equation may be utilized to determine a particular boiling point of crude oil.

$$M\%B = \{C_1 - C_2[\ln(IRxC_3)] - C_4S + C_5[1-\ln(IRxC_3)]S\}\ln KV \qquad 1.$$

where M%BP is a particular percent boiling point property, such as the 30% boiling point or the 50% boiling point, IR is the infrared absorption of the crude oil, S is the sulfur content of the crude oil, KV is the kinematic viscosity of the crude oil, and $C_1$ through $C_5$ are constants.

The particular percent boiling point to be determined by equation 1 is governed by the values of $C_1$ through $C_5$. The following Table relates 30% and 50% boiling points to the values of the constants $C_1$ through $C_5$.

|  | 30% BP | 50%BP |
| --- | --- | --- |
| $C_1$ | 550.5194 | 904.4411 |
| $C_2$ | 67.9974 | 128.9086 |
| $C_3$ | 1000.00 | 1000.00 |
| $C_4$ | 145.4940 | 263.0776 |
| $C_5$ | 31.8191 | 65.5461 |

Referring now to FIG. 1, crude oil is being fed in a line 1 through a heater 3 to a vacuum pipe still 4. It is desirable in the operation of the vacuum pipe still 4 to know the boiling point properties of the crude oil in line 1. Samples are continually drawn off through line 7 and applied to a viscosity analyzer 9, an infrared analyzer 12 and a sulfur analyzer 15 which returns the samples through line 17 to line 1. Viscosity analyzer 9, infrared analyzer 12 and sulfur analyzer 15 provide signal KV, corresponding to the kinematic viscosity of the crude oil corrected to 100° F, signal IR, corresponding to the infrared absorption of the crude oil at 6.27 microns and signal S, corresponding to the sulfur content of the crude oil, respectively.

A source of direct current voltages (not shown) provides direct current voltages $V_1$ through $V_9$. Voltage $V_1$, corresponding to the term $C_3$ in equation 1, is multiplied with signal IR by a multiplier 20 to provide a signal to a conventional type natural log function generator 23. Function generator 23 provides a signal, corresponding to the term $\ln(IRxC_3)$ to multipliers 28, 29. Multiplier 28 multiplies the signal from function generator 23 with the direct current voltage $V_2$, corresponding to the 30% boiling point constant 67.9974 ($C_2$ in equation 1) to provide a signal to summing means 33.

A multiplier 38 multiplies signal S with voltage $V_3$, corresponding to the 30% boiling point constant 145.4940 ($C_4$ in equation 1) to provide a signal to summing means 33. The signal provided by summing means 33 corresponds to the sum of all negative terms in the first equation.

Multiplier 29 multiplies the signal from function generator 23 with signal S to provide a signal, corresponding to $[\ln(IRxC_3)]S$, to a multiplier 44. Multiplier 44 multiplies the signal from multiplier 29 with voltage $V_4$, corresponding to the 30% boiling point constant 31.8191 ($C_5$ in equation 1), to provide a product signal to a summing means 46. The signal from multiplier 44 is summed with voltage $V_5$, corresponding to the 30% boiling point constant 550.5194 $C_1$ in equation 1), to provide a sum signal to subtracting means 40. Subtracting means 40 subtracts the signal provided by summing means 33 from the signal provided by summing means 46, to provide a signal to a multiplier 50. Signal KV from viscosity analyzer 9 is applied to a natural log function generator 52 which provides a signal corresponding to the term $\ln KV$ in equation 1. Multiplier 50 multiplies the signal from subtracting means 40 with the signal from function generator 52 to provide a signal $E_1$ corresponding to the 30% boiling point of the crude oil flowing in line 1.

A signal $E_2$, corresponding to the 50% boiling point of the crude oil, is also provided as follows. Signal S from sulfur analyzer 15 is multiplied with voltage $V_6$, corresponding to the 50% boiling point constant 263.0776 ($C_4$ in equation 1), by a multiplier 55 to provide a product signal. The signal from function generator 23 is multiplied with voltage $V_7$, corresponding to the 50% boiling point constant 128.9086 ($C_2$ in equation 1), by a multiplier 58 to provide a product signal to summing means 60 where it is summed with the product signal from multiplier 55.

The product signal from multiplier 29, corresponding to the term $[\ln(IR \times C_3)]S$, is applied to a multiplier 63 where it is multiplied with voltage $V_8$, corresponding to the 50% boiling point constant 65.5461 ($C_5$ in equation 1). Summing means 65 sums the signal provided by multiplier 63 with voltage $V_9$, corresponding to the constant 904.4411 ($C_1$ in equation 1), to provide a sum signal. Subtracting means 67 subtracts the signal provided by summing means 60 from the signal provided by summing means 65 to provide a signal to a multiplier 70. The signal from multiplier 70 multiplies a signal from subtracting means 67 with the signal from function generator 52 to provide signal $E_2$, corresponding to the 50% boiling point of the crude oil in line 1.

The systems hereinbefore described provide an on line determination of at least one boiling point property of crude oil. It can provide as many boiling point properties simultaneously as desired.

What is claimed is:

1. A boiling point analyzer for on-line determination of at least one boiling point property of crude oil flowing in a line comprising means for sampling the crude oil and providing samples, viscosity analyzing means receiving samples of the crude oil and providing a signal KV corresponding to the kinematic viscosity of the crude oil, infrared analyzing means connected to the sampling means and receiving a sample for providing a signal IR corresponding to the infrared absorption of the crude oil at a predetermined wavelength, sulfur analyzing means connected to the sampling means and receiving a sample for providing a signal S corresponding to the sulfur content of the crude oil, and boiling point signal means connected to all the analyzing means for providing a boiling point signal corresponding to a boiling point property of the crude oil.

2. A boiling point analyzer as described in claim 1 in which the boiling point signal means provides the boiling point signal in accordance with the following equation:

$$M\%BP = \{C_1 - C_2[\ln(IR \times C_3)] - C_4S + C_5[\ln(IR \times C_3)]S\}\ln(KV)$$

where M%BP is a particular boiling point property of the crude oil, IR is the infrared absorption of the crude oil at the predetermined wavelength, S is the sulfur content of the crude oil, KV is the kinematic viscosity of the crude oil, and $C_1$ through $C_5$ are constants.

3. A boiling point analyzer as described in claim 2 in which M%BP is the 30% boiling point and the constants $C_1$ through $C_5$ have the values of 550.5194, 67.9974, 1000, 145.4940 and 31,8191, respectively.

4. A boiling point analyzer as described in claim 2 in which M%BP is the 50% boiling point and the constants $C_1$ through $C_5$ have values of 904.4411, 128.9086, 1000, 263.0776 and 65.5461, respectively.

5. A boiling point analyzer as described in claim 2 further comprises second boiling point signal means for providing a second boiling point signal corresponding to a second boiling point property of the crude oil in accordance with the equation and in which the constants $C_1$, $C_2$, $C_4$ and $C_5$ have one set of values for the first boiling point property and another set of values for the second boiling point property.

6. A boiling point analyzer described in claim 5 in which one of the boiling point signal means provides a signal corresponding to the 30% boiling point of the crude oil as its boiling point signal in accordance with the equation where the constants $C_1$ through $C_5$ have values of 550.5194, 67.9974, 1000, 145.4940 and 31,8191, respectively, and the other boiling point signal means provides a signal corresponding to the 50% boiling point as its boiling point signal in accordance with the equation where $C_1$ through $C_5$ have values of 904.4411, 128.9086, 1000, 263.0776 and 65.5461, respectively.

* * * * *